(12) United States Patent
Gupta et al.

(10) Patent No.: US 10,895,540 B1
(45) Date of Patent: Jan. 19, 2021

(54) TOMOGRAPHIC IMAGING SYSTEM

(71) Applicant: United States of America as represented by the Administrator of NASA, Washington, DC (US)

(72) Inventors: Rajiv Gupta, Greenbelt, MD (US); Wolfgang Krull, Boxford, MA (US); Jake Hecla, Cambridge, MA (US); Avilash Cramer, Cambridge, MA (US); Steven Kenyon, Greenbelt, MD (US); Zaven Arzoumanian, Greenbelt, MD (US); Keith Gendreau, Greenbelt, MD (US)

(73) Assignee: United States of America as represented by the Administrator of NASA, Washington, DC (US)

( * ) Notice: Subject to any disclaimer, the term of this patent is extended or adjusted under 35 U.S.C. 154(b) by 0 days.

(21) Appl. No.: 16/406,300

(22) Filed: May 8, 2019

Related U.S. Application Data

(60) Provisional application No. 62/668,464, filed on May 8, 2018.

(51) Int. Cl.
| | | |
|---|---|---|
| *G01N 23/046* | (2018.01) | |
| *G06T 11/00* | (2006.01) | |
| *G01T 1/29* | (2006.01) | |
| *A61B 6/00* | (2006.01) | |
| *A61B 6/02* | (2006.01) | |
| *A61B 6/03* | (2006.01) | |

(52) U.S. Cl.
CPC .......... *G01N 23/046* (2013.01); *A61B 6/027* (2013.01); *A61B 6/03* (2013.01); *A61B 6/4064* (2013.01); *A61B 6/484* (2013.01); *G01T 1/2985* (2013.01); *G06T 11/003* (2013.01); *G06T 2207/10081* (2013.01)

(58) Field of Classification Search
None
See application file for complete search history.

(56) References Cited

U.S. PATENT DOCUMENTS

| | | | |
|---|---|---|---|
| 2006/0098783 A1* | 5/2006 | Dunham | H01J 35/065 378/122 |
| 2014/0023179 A1* | 1/2014 | Oda | H04N 5/32 378/62 |
| 2019/0178821 A1* | 6/2019 | Morton | H01J 35/08 |

* cited by examiner

*Primary Examiner* — Hoon K Song
(74) *Attorney, Agent, or Firm* — Heather Goo; Bryan A. Geurts; Helen M. Galus

(57) ABSTRACT

The present invention relates to a novel, non-rotating tomographic imaging system, including a multi-source x-ray imaging module which includes multiple x-ray sources within a vacuum manifold, each equipped with a non-thermionic cathode which can reduce image scan time (and hence, motion artifacts), or delivered radiation dose, through under-sampled acquisition sequences, and without adding additional sources. The non-thermionic nature of the cathode enables rapid on/off switching of x-rays without concern as to the thermal mass or the thermal time-constant of the cathode. The modules can be flexibly interconnected to each other to allow configuration as part of a distributed ring of sources, or in other x-ray imaging geometries. Modularity provides the present invention an advantage in making it easier to debug and repair a distributed-source imaging system, such as a computed tomographic (CT) system.

43 Claims, 3 Drawing Sheets

TOMOGRAPHIC IMAGING SYSTEM

CLAIM OF PRIORITY

The present invention claims priority from U.S. Provisional Patent Application No. 62/668,464, filed May 8, 2018, the contents of which are herein incorporated by reference in their entirety.

ORIGIN OF THE INVENTION

The invention described herein was at least in-part made by an employee of the United States Government and may be manufactured or used by or for the Government of the United States of America for governmental purposes without the payment of any royalties thereon or therefor.

BACKGROUND OF THE INVENTION

1. Field of the Invention

The present invention relates to a novel, non-rotating tomographic imaging system, including a multi-source x-ray imaging module which includes multiple x-ray sources within a vacuum manifold, each equipped with a non-thermionic cathode which can reduce image scan time (and hence, motion artifacts), or delivered x-ray radiation dose, through under-sampled acquisition sequences, and without adding additional sources.

2. Description of the Related Art

Prior art continuous-operation x-ray tubes include the basic elements of: 1) a cathode tube formed by a thermionic, or less commonly, a field-emission electron source; 2) an anode that acts as a target for the electrons because it is held at a high positive potential relative to the electron source; and 3) a vacuum manifold for housing the cathode and the anode. The electric field resulting from the potential difference between the anode and the cathode draws electrons from the electron source and accelerates them toward the anode. The electron beam impinging on the target results in x-ray emission. The target may be of transmission type (designed to transmit x-rays through), or reflection type (designed to create an anisotropic source at an angle to the electron beam axis). Physically, the emission of x-rays is caused by the rapid deceleration of electrons that impact the target, by a process known as Bremsstrahlung radiation, and through characteristic radiation of outer shell electrons in the anode target. The relative contribution of Bremsstrahlung and characteristic radiation depends on tube voltage, anode material, and beam filtration. Variations on the original x-ray tube concept include liquid-cooled targets, rotating targets to spread the heat-load from the electron beam, and tubes using triode-like electron gating for pulse-control. Prior art x-ray emission technologies allow for rapidly pulsable, miniaturized x-ray sources, utilizing carbon nanotube or photo-cathode-based emission systems.

Computed tomography (CT) is the first-line imaging modality for diagnosing a wide variety of illnesses and injuries. CT is used in a variety of fields, including medical and non-destructive testing applications. For example, brain CT is the clinical standard for diagnosing many life-threatening conditions, including traumatic brain injury and stroke.

X-ray computed tomography (CT) is a volumetric imaging technique in which a three-dimensional (3D) tomographic image is reconstructed from hundreds of projection x-ray images taken at different angles around the subject using an x-ray source mounted on a rotating gantry. The results of CT scans include a data set including a large number of x-ray projections through the same cross-section at different angles. Algorithms collectively known as the inverse Radon transform, are then used to invert the projection attenuation map into a tomographic attenuation image of the cross-section.

Specifically, the rotating gantry mechanism of a CT scanner represents a considerable portion of the mass, size, and power requirements of a conventional CT scanner, hindering its application in resource-constrained environments. The rotating system's large net angular momentum further reduces its suitability in air and space applications, for example, for use on board a spacecraft, as well as in other limited transport environments.

Recently, some non-rotating concepts have been realized, using electron accelerators and a magnetically steered beam aimed at a large ring anode surrounding the target object, or a distributed ring of carbon nanotube x-ray sources. However, these applications still suffer from the inability to be used in resource and size-constrained environments.

Accordingly, a distributed, modulated x-ray source would enable CT imaging without the use of a high-speed gantry and have significant advantages over conventional computed tomography (CT) scanner in that they eschew the need for an expensive and physically massive gantry, the need to transmit data from a rotating detector to a stationary computer for reconstruction, and remove delays inherent in the mechanical motion. Such an arrangement would also allow individual control of x-ray sources, and thus, advanced and potentially dose-reducing acquisition sequences.

SUMMARY OF THE INVENTION

The present invention relates to a novel, non-rotating tomographic imaging system, including a multi-source x-ray imaging module which includes multiple x-ray sources within a vacuum manifold, each equipped with a non-thermionic cathode which can reduce image scan time (and hence, motion artifacts), or delivered x-ray radiation dose, through under-sampled acquisition sequences, and without adding additional sources.

Accordingly, the present invention provides a distributed, modulated x-ray source that would enable CT imaging without the use of a high-speed gantry and have significant advantages over conventional computed tomography, in that the present invention would eschew the expensive and physically massive gantry, the need to transmit data from a rotating detector to a stationary computer for reconstruction, and obviate the delays inherent in mechanical motion. The present invention would also allow individual control of x-ray sources, and thus, provide for advanced and potentially dose-reducing acquisition sequences.

The present invention decreases the overall weight and size of conventional tomographic systems by simplifying the system gantry, removing the rotation motor and gear system which contributes thousands of kilograms of mass, eliminates the high-bandwidth slip ring required for transferring the projection data from the rotating components to the static computer, simplifies the high-voltage distribution on the gantry (as the present invention is motion-free), and eliminates the rotating anode and elaborate cooling system that is mandated by the high power being focused on a small focal spot on the anode.

The advantages of the present invention include compact size and portability, which allows it to be deployed in a variety of settings, including in rural communities, and military or space applications, where advanced healthcare delivery is challenging. For example, in space applications, a conventional CT system is not an option, due to its weight and the fact that a rotating gantry would impart an equal and opposite torque upon the spacecraft. A lightweight, motion-free, modular tomographic imaging system of the present invention would address these issues.

In one embodiment, an x-ray source for a computed tomographic apparatus, includes: an illumination source which produces photons; and a vacuum manifold including: a quartz window through which photons pass into the vacuum manifold; a photoemission element which interacts with the photons and produces electrons via a photoelectric effect; an electron multiplier which includes a set of wound spiral capillaries made of glass, the electron multiplier which receives the electrons from the photoemission element and amplifies the electrons into an electron beam which is accelerated through a voltage; a target which receives the electron beam from the electron multiplier on a surface of the target, and emits x-rays.

In one embodiment, the illumination source is one of a light-emitting diode which emits ultraviolet light, an optical fiber, or a lamp or a laser.

In one embodiment, the photoemission element is a cathode made from a metal or a photo-sensitive bi-alkaline material.

In one embodiment, the metal of the cathode is magnesium.

In one embodiment, the electron multiplier is amplified under a multiplier bias voltage.

In one embodiment, the target is a metal, including one of tungsten, a tungsten alloy including a tungsten-rhenium alloy, molybdenum, or rhodium.

In one embodiment, the surface of the target is angled with respect to the electron beam.

In one embodiment, an angle of the target is 10-degrees to the electron multiplier and the electron beam.

In one embodiment, the target does not rotate.

In one embodiment, the x-ray source further includes a filter which selectively absorbs x-ray photons from the x-rays outputted from the target.

In one embodiment, the filter is one of a sheet of beryllium, or molybdenum.

In one embodiment, the x-ray source further includes a window disposed in the vacuum manifold, which outputs the x-rays from the target to the filter.

In one embodiment, the window is covered by one of beryllium or aluminum.

In one embodiment, the target partially extends outside of the vacuum manifold, and the x-rays impact the filter.

In one embodiment, the x-rays from the target are collimated to eliminate portions of the x-rays.

In one embodiment, the x-ray source further includes a valve which maintains the vacuum in the vacuum manifold.

In one embodiment, the x-ray source further includes: a charged particle lensing system which focuses the electron beam on the target.

In one embodiment, the x-ray source further includes a detector array; and a control circuit; wherein the filtered x-rays pass through an object to be imaged and are detected by the detector array which provides feedback to the control circuit.

In one embodiment, the control circuit includes: a printed circuit board which controls the illumination source using a plurality of switches; and a programmable microcontroller mounted on the printed circuit board and which controls pulses of the illumination source.

In one embodiment, a module for a computed tomographic apparatus, includes: a plurality of x-ray sources as described above; a modular housing; wherein a plurality of the illumination sources are disposed outside of the modular housing and each of the plurality of illumination sources illuminates each of the plurality of x-ray sources; a plurality of windows disposed in the modular housing, and corresponding to each of the plurality of illumination sources, and through which the plurality of the illumination sources illuminate the plurality of x-ray sources; and a plurality of ports disposed in the modular housing to accommodate a vacuum pump, and a plurality of voltage lines.

In one embodiment, each of the plurality of voltage lines includes a voltage line which biases each of the electron multipliers disposed in each of the x-ray sources.

In one embodiment, the module further includes a vacuum maintaining getter which seals the modular housing once a desired vacuum level is reached.

In one embodiment, the module further includes a valve which maintains the vacuum in the modular housing.

In one embodiment, a tomographic imaging system, includes: a plurality of modules as described above, the plurality of modules which are interconnected with one another and disposed in a plurality of geometries, including at least one of a 360-degree ring, a U-shaped geometry, a linear shape, or a polygonal geometry; wherein each of the plurality of x-ray sources is modulated in time and/or frequency domains using a programmable controller; and wherein the plurality of interconnected modules are synchronized with the programmable controller.

In one embodiment, the plurality of modules shares a plurality of vacuum pumps and a plurality of voltage lines.

In one embodiment, each of the plurality of modules are individually connected to an external vacuum pump and/or power supply.

In one embodiment, the control circuit triggers an electron generation process by turning on or off each of the illumination sources of each of the x-ray sources, using the programmable microcontroller, to modulate production of the x-rays from each of the plurality of x-ray sources.

In one embodiment, the programmable microcontroller enables both individual control and high-frequency pulsing of each of the plurality of x-ray sources, by switching at least the plurality of optical switches to control each of the plurality of illumination sources.

In one embodiment, the switching is performed in a predetermined pattern and temporal sequence programmed into the programmable microcontroller.

In one embodiment, the tomographic imaging system further includes an anti-scatter grid which separates transmitted photons from scattered photons.

In one embodiment, the detector array includes a plurality of single photon avalanche diodes (SPADs).

In one embodiment, a tomographic imaging system includes: a plurality of modules containing a plurality of x-ray sources in each of the plurality of modules, the plurality of modules being arranged in a plurality of geometric shapes; wherein each of the plurality of modules includes an illumination source which emits photons; wherein each of the plurality of modules includes a metallic photocathode having non-thermionic electron generation in each of the plurality of x-ray sources; an electron multiplier which amplifies electrons generated from the metallic photocathode; a metallic anode target which receives the amplified electrons and generates x-rays; and a plurality of detectors which detect the x-rays emitted from each of the plurality of x-ray sources; wherein the plurality of x-ray sources are modulated in time and/or frequency domains by a programmable controller.

In one embodiment, a method of operating a tomographic imaging system, includes: generating a plurality of x-rays from a plurality of x-ray sources disposed in a plurality of modules arranged in a plurality of geometric shapes, by: emitting photons from a plurality of illumination sources disposed in each of the plurality of modules; generating electrons from each of a plurality of metallic photocathodes having non-thermionic electron generation; wherein each of the plurality of metallic photocathodes are disposed in each of the plurality of x-ray sources, each of the plurality of metallic photocathodes which emit the electrons which are amplified by one of a plurality of electron multipliers disposed in each of the plurality of x-ray sources; generating x-rays from each of a plurality of metallic anode targets disposed in each of the plurality of x-ray sources, each of the plurality of metallic anode targets which receive the amplified electrons from one of a plurality of electron multipliers; and detecting the x-rays emitted from each of the plurality of x-ray sources in the plurality of x-ray modules, using a plurality of detectors disposed adjacent to the plurality of modules; and modulating each of the plurality of x-ray sources in time and/or frequency domains using a programmable controller.

In one embodiment, the method further includes turning on or off the plurality of x-ray sources to provide a coded pattern or temporal sequence of x-ray illumination.

In one embodiment, the coded pattern is used to modulate a radiation dose delivered to each portion of an object to be imaged.

In one embodiment, when multiple of the plurality of x-ray sources are turned on at a same time in a ring geometry of the plurality of modules, fields of view of said plurality of x-ray sources do not overlap, and any non-overlapped projections are acquired simultaneously.

In one embodiment, the method further includes implementing a partitioning scheme to determine which of the x-rays incident on one of the plurality of detectors originates from which of the plurality of x-ray sources, when the plurality of x-ray sources are turned on at the same time.

In one embodiment, each of the x-ray sources allows encoding of any arbitrary waveform in an X-ray domain.

In one embodiment, the illumination from the plurality of x-ray sources is disjointed in time.

In one embodiment, the partitioning scheme allows for blind source separation of the plurality of x-ray sources illuminating a same detector of the plurality of detectors.

In one embodiment, each of the plurality of sources is operated at one of a plurality of frequencies which distinguishes overlapping signals received by a detector from a plurality of detectors.

In one embodiment, the method further includes combining the plurality of modules with other imaging systems to achieve ultra-low dose radiographic imaging.

In one embodiment, the method further includes providing, in real-time, response times and a current draw of each of the illumination sources.

In one embodiment, the method further includes modulating the x-rays by controlling the generation of electrons in each of the plurality of sources, using a control computer; wherein the control by the control computer is accomplished by enabling individual control and high-frequency pulsing of each of the plurality of x-ray sources.

In one embodiment, recording of images of an object to be imaged, is performed by the plurality of x-ray sources from multiple angles simultaneously, to reduce a scan time or a delivered radiation dose through under-sampled acquisition sequences.

Thus, has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

The description of the drawings includes exemplary embodiments of the disclosure and are not to be considered as limiting in scope.

DESCRIPTION OF THE INVENTION

The present invention relates to a novel, non-rotating tomographic imaging system, including a multi-source x-ray imaging module which includes multiple x-ray sources within a vacuum manifold, each equipped with a non-thermionic cathode which can reduce image scan time (and hence, motion artifacts), or delivered dose, through under-sampled acquisition sequences, and without adding additional sources. The non-thermionic nature of the cathode enables rapid on/off switching of x-rays without concern as to the thermal mass or the thermal time-constant of the cathode.

In one embodiment, the x-ray sources of the present invention are encapsulated in a modular housing that is kept at vacuum. The modules can be flexibly interconnected to each other. Such flexibility enables these multi-source x-ray modules to be configured as part of a distributed ring of sources, or in other x-ray imaging geometries. For example, one could obtain a ring, ellipse, or other three-dimensional (3D) geometry, in addition to a 2D geometry (flat panel) depending on the application. In one embodiment, a partial ring could be used for chest, breast, or limb tomosynthesis. In one embodiment, a small ring of lower energy sources could be used for neuroimaging. In one embodiment, a large ring of 120-150 kVp sources could be used for whole body tomography. In one embodiment, a U-shape could be used for non-destructive testing. Each source is to be itself modular such that they may be individually connected and disconnected from the vacuum manifold.

Modularity provides the present invention an advantage in making it easier to debug and repair a distributed-source imaging system, such as a computed tomographic (CT) system. Furthermore, a modular, multi-source x-ray element would be a flexible use component in a variety of systems and applications beyond medical tomography alone.

Figure 1:
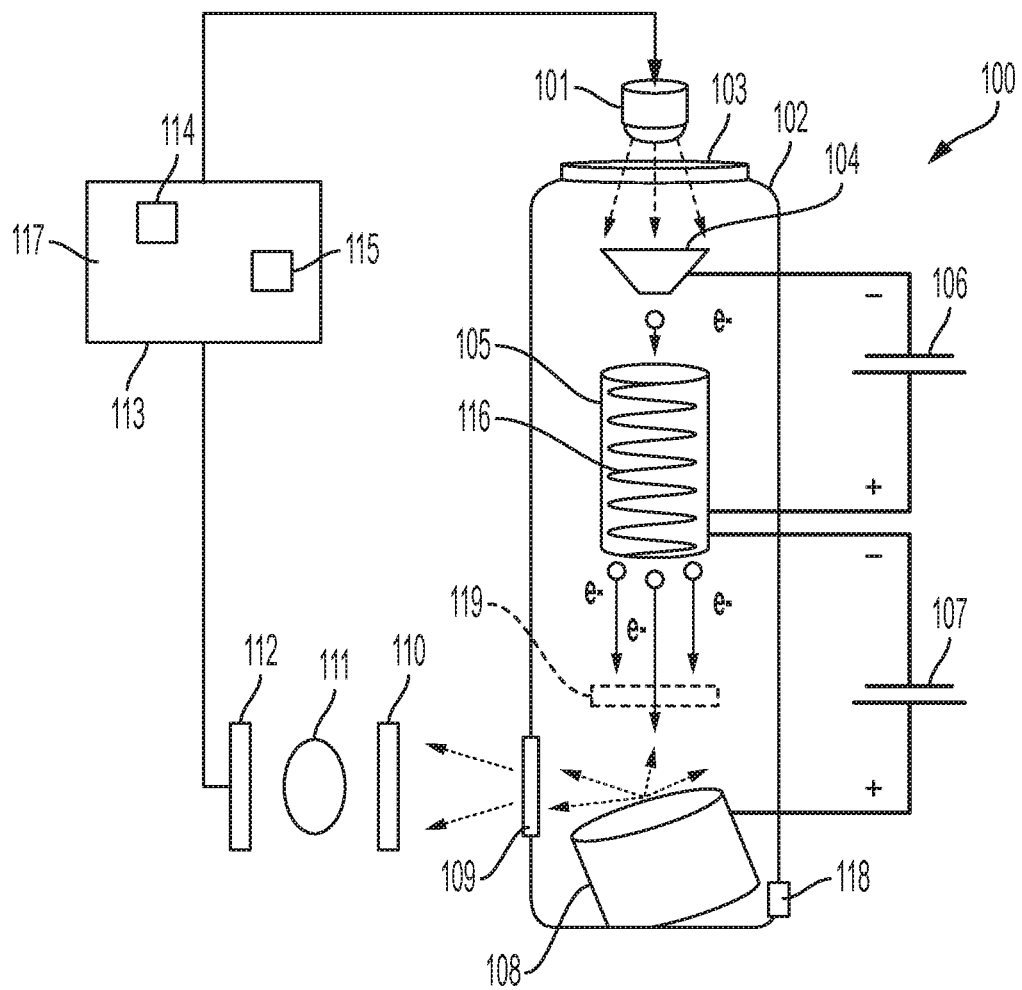
FIG. 1 depicts a schematic diagram of a photocathode according to one embodiment consistent with the present invention.

In one embodiment, as shown in FIG. 1, x-ray generation is accomplished by a photocathode or field emission-based x-ray source 100.

In one embodiment, since light-emitting diodes (LEDs) are able to tolerate high frequency switching, an illumination source 101, such as a rapidly pulsable, individually controlled LED 101, or individually switched optical fibers connected to a lamp or laser, is used to illuminate the photocathode 100. In one embodiment, the LED is an ultraviolet (UV) light (about 255 nm wavelength) which produces UV photons which pass into a vacuum manifold 102 via a quartz window 103. The UV photons emitted by the LED 101 interact with a photoemission element (for example, a funnel) 104.

In one embodiment, a valve 118 allows the vacuum to be maintained by connection to a vacuum pump (not shown in FIG. 1).

In one embodiment, the photoemission element or cathode 104 is a metallic cathode 104, which is used in the x-ray imaging module 200 (see FIG. 2) of the tomographic imaging system. Metallic photocathodes 104 are robust, easy to deposit, have a long lifetime, and can survive being briefly brought up to atmospheric pressure. They are also intrinsically radiation hard and feature a sub-picosecond response time for fast pulsing.

In one embodiment, the cathode 104 is magnesium, where magnesium 104 (i.e., a magnesium film) is exposed to ultraviolet (UV) light from the illumination source 101 to produce electrons (e⁻) via the photoelectric effect. Magnesium has a relatively high quantum efficiency (QE) at the chosen UV wavelength, is very abundant, and has relatively few special handling concerns. In addition to magnesium, other metals or photo-sensitive bi-alkaline materials 104 which have a similar response at different frequency profiles, may also be used.

Similarly, in an alternative embodiment, field emission could be used to generate electrons, by exposing a set of nano-sharp tips (not shown) to an electric field that overcomes the work function of the material of the cathode 104. Both photo and field emission x-ray sources have the desirable property that they can be turned on or off rapidly.

In one embodiment, the electrons which pass through the photoemission element 104, are received by a multi-channel plate or electron multiplier 105, such as a Channeltron™-type device 105, and amplified under a multiplier bias voltage 106 of approximately 3 kV. Electron amplification multiplies the number of electrons produced in the electron generation stage by the Channeltron™-type device 105.

Since human imaging typically requires hundreds of milliamperes of x-ray tube current, to amplify the photocurrent, in one embodiment, a Channeltron™ electron multiplier 105 (i.e., a Magnum 5900) with an adjustable bias voltage of 2500 to 4000 V may be used. Originally developed for mass spectrometry, a Channeltron™ 105 includes a set of tightly wound spiral capillaries 116. The capillaries 116 are coated with an emissive layer of an appropriate material (i.e., doped black glass) and supplied with a bias voltage that propels the injected electrons forward. The electrons produced by photoemission are injected into the input end of these capillaries 116. They bounce repeatedly from the walls of the Channeltron™, 105 with each interaction producing more electrons, before they exit from the output end towards the target 108.

The Channeltron™ 105 amplifies the current produced by the photocathode 104 on its input surface by a factor of up to 108. As a result, the individual source elements can produce up to 1 mA of tube current. This tube current can be modulated by changing the bias voltage or input illumination of the Channeltron™ 105.

In one embodiment, after amplification, the increased number of electrons from the Channeltron™ 105 result in an amplified electron beam which is then accelerated through a high voltage 107—10-40 kv, for example—and is incident upon a target 108. Specifically, the electrons outputted from the Channeltron™ 105 are accelerated as they fall down the voltage gradient between the cathode and anode. In medical x-ray tomography, typically tube voltages are between 22 kVp (digital breast tomography) and 140 kVp (such as in a pelvic CT). The voltage level of the anode determines the energy spectrum of the x-rays produced by the source 108. Alternatively, electrons can be accelerated using a set of resonant radio frequency (RF) cavities, especially if higher voltages (6-25 MVp) are desired.

In one embodiment, between the amplification stage (device 105) and hitting the target 108, the electron beam can be focused on to the target 108 using a modulated electric or magnetic field, or a charged-particle lensing apparatus, such as an Einzel lensing system 119. In one embodiment, the Einzel lensing system 119 may include a series of electrostatic lenses at the output of the Channeltron™.

In one embodiment, the material of the anode target 108 may be metal, such as tungsten, a tungsten alloy including a tungsten-rhenium alloy, molybdenum, rhodium, or other material with a high atomic number. In one embodiment, a tungsten anode rod 108 is held in place by screws in the manifold 102.

The electron beam from the amplification stage 105 interacts with this target 108, which produces the high energy x-rays. Specifically, accelerated electrons striking a metal target 108 will emit x-rays over a range of energies dependent on the energy of the incident electrons and the energy levels of various electron shells of the target material 108.

In the present invention, both transmission-type, as well as reflection-type of x-ray generation, is feasible. In the latter arrangement, in one embodiment, the anode surface of the target 108 is angled with respect to the incident electron beam in order to control the cone angle of the emitted x-rays.

In one embodiment, the target 108 is set at a 10-degree angle to the electron multiplier (i.e., Channeltron™) 105 and the electron beam therefrom. This reduces the projected spot size in one dimension, creating an ellipse. Because the heat is deposited at multiple anode targets 108 of multiple x-ray sources 100 in the present invention, there is no need to physically rotate the individual targets 108 for cooling.

In one embodiment, the target 108 is designed to have a high thermal mass. It does not need to rotate, and in an alternative embodiment, a part of it may extend outside the vacuum manifold 102 for direct cooling. The overall arrangement can be described as distributed-cathode/static-anode arrangement, unlike the conventional cathode tube that has a single, static-cathode/rotating-anode arrangement.

In one embodiment, the x-ray output emanating from the target 108 comes out of the vacuum manifold 102 through a window 109 that is nearly x-ray transparent. In one embodiment, the window 109 may be covered with a thin, low atomic number element such as beryllium or aluminum. In one embodiment, a beryllium window 109 is used for its low atomic number (z–4) and relative stability in atmosphere.

In one embodiment, the x-rays from the target 108, once through the x-ray window 109, may be filtered by a filter 110 to achieve beam hardening by selectively absorbing low-energy x-ray photons from the output x-rays. Depending on the application, in one embodiment, the filter 110 could be a thin sheet of beryllium, molybdenum, or other material.

In one embodiment, the x-rays may be collimated to eliminate the portions of the x-ray beam that are not required for the application.

In an alternative embodiment, the anode target 108 is transmissive, rather than reflective, and the window 109 is omitted. In that case, as noted above, the target 108 can partially extend outside the vacuum manifold 102 for external cooling, and the x-rays from the target 108 can impact the filter 110 directly.

In one embodiment, the filtered x-rays pass through the object 111 to be imaged (for instance, a patient), and are recorded by a detector array 112 which provides feedback to a control circuit 113.

In one embodiment, the control circuit 113 includes a printed circuit board (PCB) 117 which controls the illumination source (i.e., UV LED) 101, and which has two separate circuits: a 20V power line and a 5V logic line. In one embodiment, the circuit 113 uses a board-mounted microprocessor 114 to control the pulses of the UV LEDs 101 through a bi-polar junction transistor (BJT) (not shown). In one embodiment, the microcontroller 114 switches a series of transistors, opto-isolators, optical switches, or other high-speed switches 115 to control the illumination sources (i.e., LEDs) 101.

In one embodiment, the 5V logic lines are kept protected to ground and separated from the 20V power lines by opto-isolators. In one embodiment, a constant current is provided to the LEDs 101 by two constant current diodes (CCRs) in parallel (not shown). In one embodiment, these CCRs limit the current to a maximum of 100 mA to protect the LEDs 101, which are 100 mA. However, in one embodiment, the current provided by the CCRs can be adjusted by a potentiometer (not shown) in series with one of the CCRs.

In one embodiment, a visible indicator LED (not shown) is disposed in parallel with each UV LED 101. In one embodiment, a high-side current sense chip (i.e., LT1787 model) (not shown) provides feedback from each LED circuit to the microprocessor 114, and allows monitoring, in real-time, the response times and current draw of the UV LED 101. In one embodiment, four-pin phoenix connectors (not shown) on the top of the circuit board 113 enable transmission and reception of timing signals from the flat-panel detector and other equipment.

Figure 2:
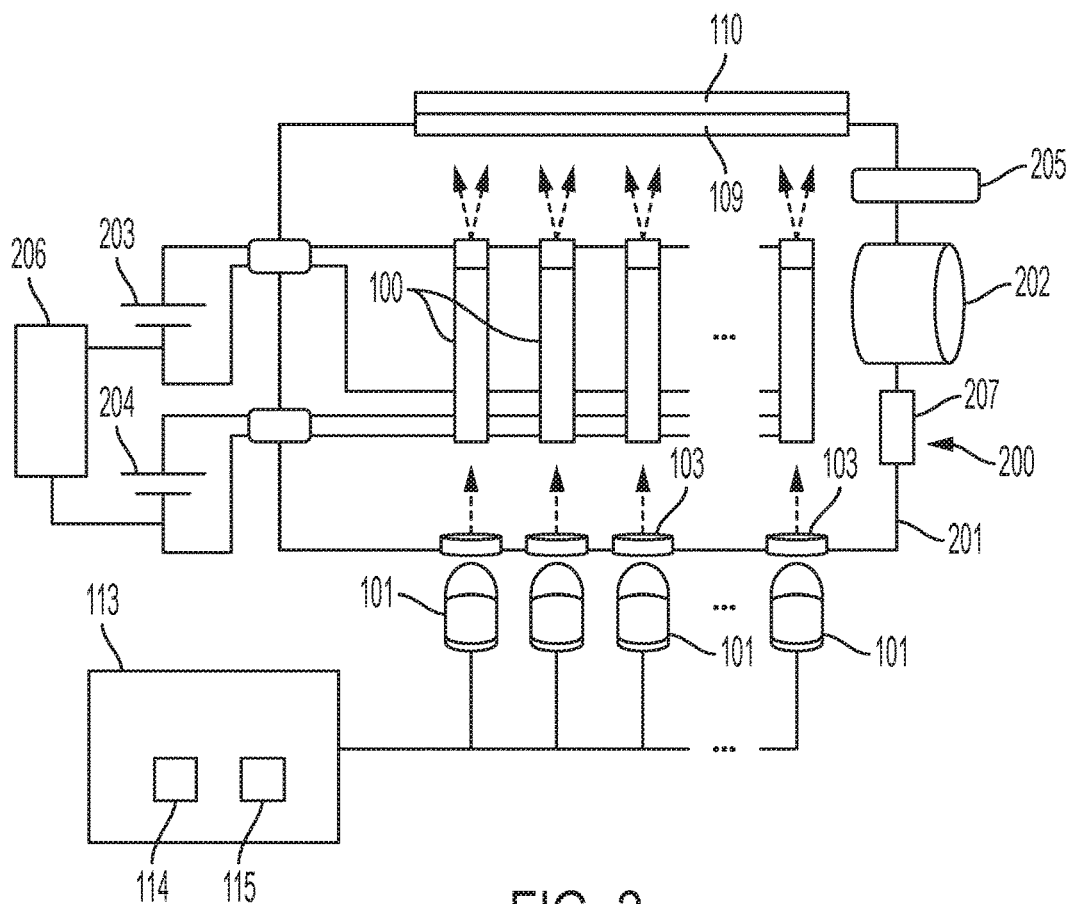
FIG. 2 depicts a schematic diagram of an n-element module of a tomographic imaging system, according to one embodiment consistent with the present invention.

FIG. 2 shows an exemplary embodiment of an n-element module 200. In the module 200, in one embodiment, multiple individual sources 100 are packaged into a lightweight modular housing 201. In one embodiment, illumination sources 101 such as LEDs 101 or optical fibers, provide illumination for the UV-to-x-ray subassembly of individual sources 100 through (quartz) windows 103.

In one embodiment, the housing 201 contains ports for a lock-on vacuum connection (i.e., vacuum pump 202), the anode high voltage 203 line, a separate high voltage line 204 for the biasing the electron multiplier 105 within the source 100, and an optional vacuum maintaining getter 205 for sealing the housing 201 permanently once the desired vacuum is reached.

In one embodiment, a vacuum in the housing 201 is provided by a turbopump 202 or other vacuum pump 202. A vacuum flange or port on the rear of the housing 201 allows for the housing 201 to be connected to the turbopump 202. In one embodiment, a valve 207 allows the vacuum to be maintained even when separated from the turbopump 202. Alternatively, in one embodiment, a vacuum may be provided during the module 200 assembly process, such as during manufacturing, and permanently maintained by sealing the vacuum manifold.

Unlike conventional tomographic (CT) devices, the present invention does not require an ultra-high vacuum, and a $10^{-6}$ to $10^{-7}$ Torr may be used and should survive exposure to full atmospheric pressure for short durations, allowing for easy repair and replacement within the housing.

Figure 3:
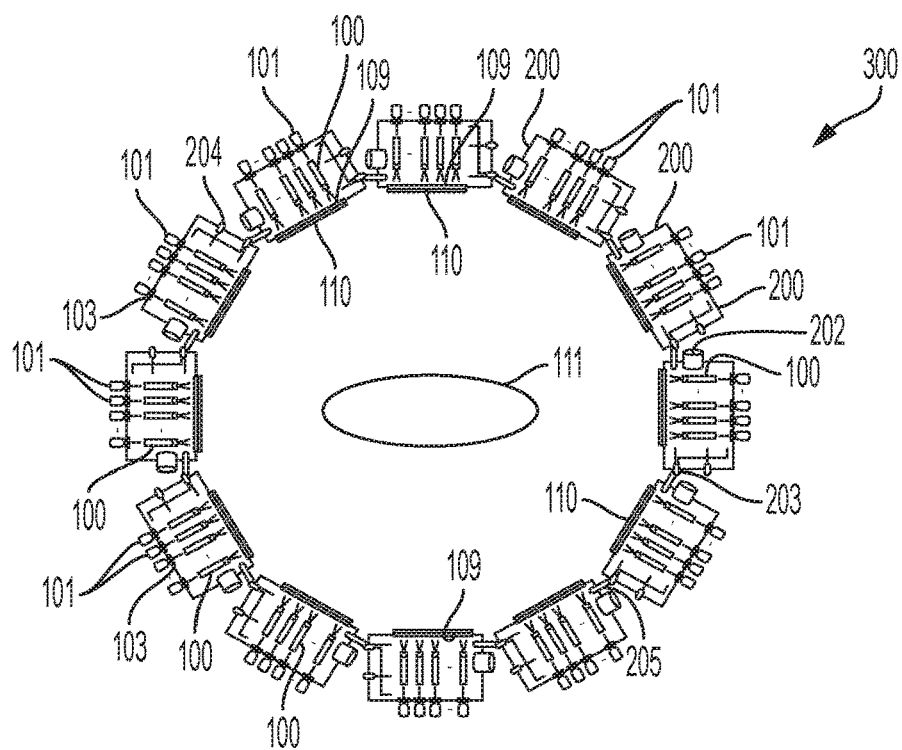
FIG. 3 depicts a schematic diagram of a 360-degree ring of the n-element modules of FIG. 2, according to one embodiment consistent with the present invention.

In one embodiment, as shown in FIG. 3, the modules 200 can be interconnected, sharing vacuum and high voltage inputs, or in another embodiment, each module 100 can be individually connected to an external vacuum pump and/or power supply (not shown). Regardless of how the modules are assembled, each x-ray source 100 remains individually addressable by the control system 113.

In one embodiment, as shown in FIG. 2, the external control circuit 113 allows for individual control of each light source 101, and thereby, each x-ray source.

In one embodiment, an external controller 208, which executes control software, is used to control the acceleration, bias, and other high voltage connections. In one embodiment, a digital/analog input/output (IO) device (not shown), such as a LabJack UE9 digital/analog IO device, is used to control three separate low voltage power supplies and a series of relays, which in turn control the output of high voltage power supplies. In one embodiment, the hardware connections are made through a printed circuit board (PCB) 206. In one embodiment, in addition to the presence of two separate emergency stop buttons, all of the switches and software controls are designed to fail safe through relays and gas discharge tubes. In one embodiment, a control program, such as LabView, is used to control, monitor and record the current and voltage of these sources in real time. In one embodiment, the control program allows for synchronization pulses to be sent to coordinate with external hardware devices, such as the flat panel detector of the tomographic imaging system. In one embodiment, the control system is used to simultaneously control and adjust a 10-50 kV circuit and a 1-5 kV circuit.

Figure 4A:
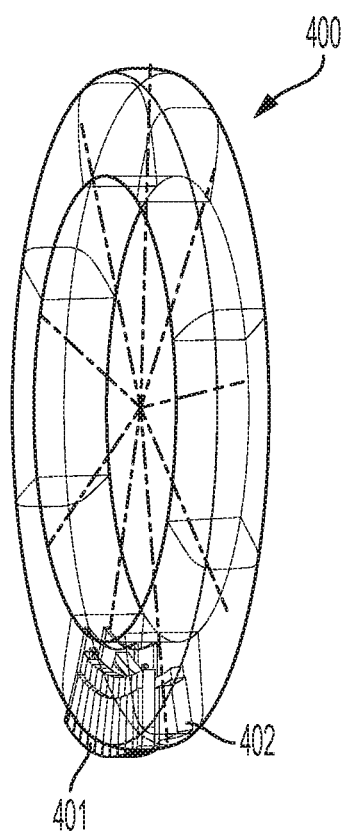
FIG. 4A depicts a schematic diagram of a 360-degree ring of n-element modules of FIG. 2 and detectors in arrays.
Figure 4B:
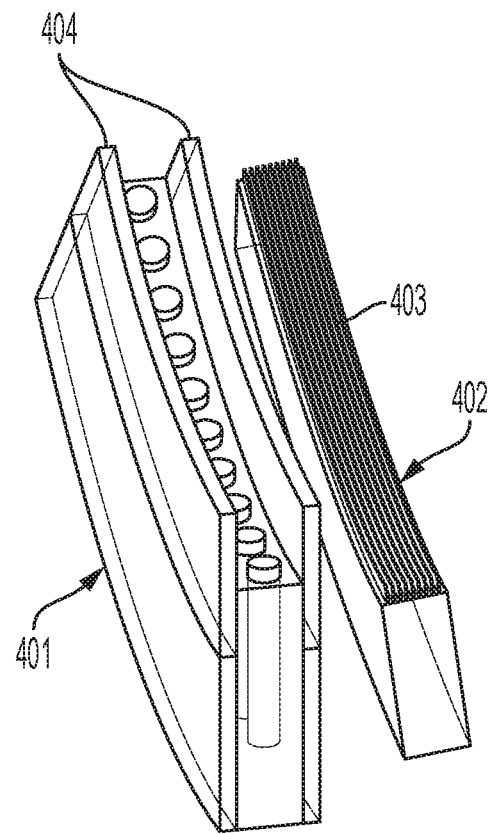
FIG. 4B depicts the n-element module and detector array with anti-scatter grid, according to one embodiment consistent with the present invention.

In one embodiment, the controller 113 may derive feedback from the image cast upon the detector (see detector array 402) (see FIGS. 4A-4B), in order to optimize the x-ray illumination schedule, for example, for automatic brightness control or low-dose operation. The x-ray sources 100 emit x-rays from the target 108 and pass through the window 109 and filter stage 110.

More specifically, in operation, in one embodiment, digital control of individual x-ray sources 100 is achieved by an integrated control computer 113 that triggers the electron generation process. By turning on and off the UV light 101 of each source 100, the control computer 113 modulates the x-ray production from each individual source 100.

In an exemplary implementation, this type of control could be accomplished by a programmable microcontroller 114 to enable both individual control and high-frequency pulsing of the x-ray sources 100.

In alternative embodiments, an optical switching arrangement can be provided where the x-ray sources 100 are driven by a laser pulses from a laser (not shown) instead of an LED 101. In this embodiment, the switches 115 would modulate the light transmission rather than the light generation.

In one embodiment, a single controller 113 may be used for multiple LEDs 101, and by extension, multiple x-ray sources 100. Such synchronization of x-ray sources 100 enables coded operation where a subset of the sources 100 are turned on, according to a predetermined pattern and temporal sequence programmed into the controller 113.

In one embodiment, the x-ray sources of the present invention can be arbitrarily and simultaneously turned on or off to provide for any coded pattern, which patterns can be employed for scanning and reconstruction of tomographic images.

In one embodiment, detection of the x-ray images is achieved by a modular detector array 402 (see FIGS. 4A-4B) that can be integrated or separately connected to the source array 40 (in a 360-degree ring 400, for example), and synchronized with the control board 113. In one embodiment, the detector array 402 itself could be assembled to form complex structures with the x-ray sources 401, which include—in addition to a 360-degree ring 400 (see FIGS. 3-4)—a U-shaped geometry that covers 180-degrees plus the cone angle of x-rays, a linear shape for tomosynthesis, polygonal geometry for non-traditional applications such as baggage scanning, or other geometries. This modularity is a great advantage for disassembly and portability of the present invention.

In one embodiment, the detector array 402 is a Varex Imaging 2530DX flat panel detector, which is synchronized with the control board 113.

In one embodiment, a linear or partial ring configuration of the present invention is used for tomosynthesis imaging or 3D CT imaging, such as for mammography applications. A partial or full ring of sources 401 and detectors 402 could be used for CT imaging by individually controlling one or more sources 401 and sequentially enabling them to illuminate the object to be imaged. Acquired images can then be reconstructed using 3D reconstruction algorithms such as the Fieldkamp-Davis-Kress (FDK), iterative reconstruction algorithms, or modern machine learning techniques.

In one embodiment, being able to control every source 100 individually and simultaneously also allows for advanced illumination sequences and fluoroscopic imaging or radiography. By recording images of the object to the imaged from multiple angles simultaneously, it may be possible to reduce the scan time (and hence motion artifact) or delivered dose through under-sampled acquisition sequences.

In one embodiment, to reduce scan times (if sufficient flux is achieved), the x-ray source pulse rate can be increased. A faster pulse rate will allow for faster scan times in tomographic imaging. In one embodiment, if the x-ray source pulse rate was reduced to the order of nanoseconds (well within the reach of a metallic photocathode which has a sub-picosecond response time), time-domain x-ray imaging, with the potential for a dramatic reduction in delivered radiation dose, is feasible.

Additionally, in one embodiment, an array of source modules 401 on a static or movable ring (see FIGS. 4A-4B) or linear stage would allow for image acquisition from even more illumination angles without adding additional sources. The number, size, and orientation of the source modules 400 are flexible as long as they achieve the needs of the user, but should be lightweight, and energy efficient. Depending on application, either a flat panel or curved detector may be used. The detector array 402 could incorporate an anti-scatter grid 403, post-processing scatter rejection, or other scatter compensation hardware or software in order to separate transmitted photons from scattered photons. A scatter compensation scheme will be especially important in an acquisition sequence where multiple sources 100 are simultaneously emitting. Finally, overall shielding 404 requirements for the present invention do not differ from that of conventional CT systems and can be tailored to suit requirements.

To increase image quality over conventional CT systems, one of ordinary skill in the art would know that various techniques could be used, including at least one of increasing the active surface area of the electron multipliers, optimizing the photocathode deposition process, increasing the multiplier bias voltage, and replacing the UV LEDs with switched UV lamps (i.e., 180 nm UV lamp).

In one embodiment, in operation of the present invention, the x-ray sources 100 of the present invention can be arbitrarily and simultaneously turned on or off, and change their tube current, in order to provide for any coded pattern of x-ray illumination. Such coded patterns can be employed for scanning and reconstruction of tomographic images. Coded illumination patterns could also be used to precisely modulate the radiation dose delivered to each portion of the imaged object, which could lead to an overall radiation dose reduction.

In one embodiment, because individual sources 100 can be modulated individually, multiple sources 100 can be on at the same time. In one embodiment, multiple sources 100 in a ring are turned on simultaneously so that their fields of view do NOT overlap (for example, if each source module 200 illuminated a 60-degree arc angle). In one embodiment, such non-overlapped projections can be acquired simultaneously (thereby reducing the overall scan time) and reconstructed using conventional tomographic reconstruction algorithms.

In one embodiment, a partitioning scheme can be implemented by the control software, to determine which photons incident on a detector pixel originated from which source when that individual detector (see detector array 402) is illuminated by multiple x-ray sources 100 in the modules 200 at the same time. In one embodiment, the partitioning scheme also partitions the Compton scattered photons. In one embodiment, the rapid on/off capability of each x-ray source allows encoding of any arbitrary waveform in the X-ray domain. In one embodiment, many different encoding and multiplexing schemes could be used. In one embodiment of the encoding scheme, the x-ray sources 100 could be turned on so that the illumination patterns they generate are disjointed in time. Such a time-domain multiplexing is routinely used in signal communication and in radio transmission. In one embodiment, time division multiplexing (TDM) can be applied to x-ray illumination and reconstruction.

In another embodiment of coded-source illumination, each source can be operated at different frequencies and different techniques used from frequency domain multiplexing to disambiguate different overlapping signals received by a detector 402.

In one embodiment, contrary to standard radio transmission, where the carrier frequencies are known and an unknown, time-varying signal is extracted from each channel, in the present invention, the carrier frequency and time-varying baseband signal are known completely. By comparing the magnitude of the recovered baseband signals to the original signal, the attenuation can be known. In other embodiments, other encoding and decoding schemes such as Hadamard encoding, statistical time-division multiplex, or variants thereof, may be used.

In one embodiment, utilizing arrays of single photon avalanche diodes (SPADs) as detectors, the present invention could be combined with other systems to achieve ultra-low dose radiographic imaging. Such a configuration would exploit the picosecond timing resolution of the SPADs to measure the temporal statistics of incident x-ray photons. This would allow for first-photon and time-off-flight imaging, which would allow for x-ray imaging in the single photon regime.

In another advantage, the compact modular structure of the present invention makes it easier to combine with other medical equipment such as the positron emission tomography (PET) for simultaneous PET/CT imaging, or the Magnetic Resonance (MR) scanner for a portable MR/CT system.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A module for a computed tomographic apparatus, comprising:
    a plurality of x-ray sources, each x-ray source including:
        an illumination source which produces photons;
        a vacuum manifold including:
            a quartz window through which said photons pass into said vacuum manifold;
            a photoemission element which interacts with said photons and produces electrons via a photoelectric effect;
            an electron multiplier which includes a set of wound spiral capillaries, said electron multiplier which receives said electrons from said photoemission element and amplifies said electrons into an electron beam which is accelerated through a voltage; and
            a target which receives said electron beam from said electron multiplier on a surface of said target, and emits x-rays; and
    a modular housing, wherein
        a plurality of said illumination sources are disposed outside of said modular housing and each of said plurality of illumination sources illuminates each of said plurality of x-ray sources;
        a plurality of windows disposed in said modular housing, and corresponding to each of said plurality of illumination sources, and through which said plurality of illumination sources illuminate said plurality of x-ray sources;
        a plurality of ports disposed in said modular housing to accommodate a vacuum pump and a plurality of voltage lines.

2. The module of claim 1, wherein each said illumination source is at least one of a light-emitting diode which emits ultraviolet light, an optical fiber, a lamp or a laser.

3. The module of claim 1, wherein each said photoemission element is a cathode made from a metal or a photosensitive bi-alkaline material.

4. The module of claim 3, wherein said metal of said cathode is magnesium.

5. The module of claim 1, wherein each said electron multiplier is amplified under a multiplier bias voltage.

6. The module of claim 5, wherein each said target is a metal, including one of tungsten, a tungsten alloy including a tungsten-rhenium alloy, molybdenum, or rhodium.

7. The module of claim 6, wherein said surface of said target is angled with respect to said electron beam.

8. The module of claim 7, wherein an angle of said target is 10-degrees to said electron multiplier and said electron beam.

9. The module of claim 8, wherein said target does not rotate.

10. The module of claim 1, wherein said plurality of x-ray sources comprises:
    at least one filter which selectively absorbs x-ray photons from said x-rays outputted from said target.

11. The module of claim 10, wherein said filter is one of a sheet of beryllium, or molybdenum.

12. The module of claim 10, wherein said plurality of x-ray sources comprises:
    at least one window disposed in said vacuum manifold, which outputs said x-rays from said target to said filter.

13. The module of claim 12, wherein said window is covered by one of beryllium or aluminum.

14. The module of claim 10, wherein each said target partially extends outside of said vacuum manifold, and said x-rays impact said filter.

15. The module of claim 10, wherein said x-rays from said targets are collimated to eliminate portions of said x-rays.

16. The module of claim 1, the module further comprising:
    a valve which seals said modular housing once a predetermined vacuum level is reached.

17. The module of claim 1, wherein each x-ray source further includes:
    a charged particle lensing system which focuses said electron beam on said target.

18. The module of claim 1, the module further comprising:
    a detector array; and
    a control circuit;
    wherein a plurality of filtered x-rays pass through an object to be imaged and are detected by said detector array which provides feedback to said control circuit.

19. The module of claim 18, wherein said control circuit includes:

a printed circuit board which controls said illumination source using a plurality of switches; and a programmable microcontroller mounted on said printed circuit board and which controls pulses of said illumination source.

20. The module of claim 1, wherein each of said plurality of voltage lines includes a voltage line which biases each of said electron multipliers disposed in each of said x-ray sources.

21. The module of claim 1, the module further comprising:

a vacuum maintaining getter which maintains said vacuum in said vacuum manifold.

22. A tomographic imaging system, the tomographic imaging comprising:

a plurality of modules, each module including:
  a plurality of x-ray sources, each x-ray source including:
    an illumination source which produces photons;
    a vacuum manifold including:
      a quartz window through which said photons pass into said vacuum manifold;
      a photoemission element which interacts with said photons and produces electrons via a photoelectric effect;
      an electron multiplier which includes a set of wound spiral capillaries, said electron multiplier which receives said electrons from said photoemission element and amplifies said electrons into an electron beam which is accelerated through a voltage; and
      a target which receives said electron beam from said electron multiplier on a surface of said target, and emits x-rays;
  a modular housing;
  wherein a plurality of said illumination sources are disposed outside of said modular housing and each of said plurality of illumination sources illuminates each of said plurality of x-ray sources;
  a plurality of windows disposed in said modular housing, and corresponding to each of said plurality of illumination sources, and through which said plurality of said illumination sources illuminate said plurality of x-ray sources; and
  a plurality of ports disposed in said modular housing to accommodate a vacuum pump and a plurality of voltage lines,
  said plurality of modules being interconnected with one another and disposed in a plurality of geometries, including at least one of a 360-degree ring, a U-shaped geometry, a linear shape, or a polygonal geometry;
wherein each of said plurality of x-ray sources is modulated in time and/or frequency domains using a programmable controller; and
wherein said plurality of interconnected modules are synchronized with said programmable controller.

23. The tomographic imaging system of claim 22, wherein said plurality of modules share a plurality of vacuum pumps and a plurality of voltage lines.

24. The tomographic imaging system of claim 22, wherein each of said plurality of modules are individually connected to an external vacuum pump and/or power supply.

25. The tomographic imaging system of claim 22, wherein said control circuit triggers an electron generation process by turning on or off each of said illumination sources of each of said x-ray sources, using said programmable microcontroller, to modulate production of said x-rays from each of said plurality of x-ray sources.

26. The tomographic imaging system of claim 25, wherein said programmable microcontroller enables both individual control and high-frequency pulsing of each of said plurality of x-ray sources, by switching at least said plurality of optical switches to control each of said plurality of illumination sources.

27. The tomographic imaging system of claim 26, wherein said switching is performed in a predetermined pattern and/or temporal sequence programmed into said programmable microcontroller.

28. The tomographic imaging system of claim 22, the tomographic imaging system further comprising:

an anti-scatter grid which separates transmitted photons from scattered photons.

29. The tomographic imaging system of claim 22, wherein said detector array includes a plurality of single photon avalanche diodes (SPADs).

30. A tomographic imaging system, the tomographic imaging system comprising:

a plurality of modules containing a plurality of x-ray sources in each of said plurality of modules, said plurality of modules being arranged in a plurality of geometric shapes;
  wherein each of said plurality of modules includes at least one illumination source which emits photons;
  wherein each of said plurality of modules includes a metallic photocathode having non-thermionic electron generation in each of said plurality of x-ray sources;
an electron multiplier which amplifies electrons generated from said metallic photocathode;
a metallic anode target which receives said amplified electrons and generates x-rays; and
a plurality of detectors which detect said x-rays emitted from each of said plurality of x-ray sources;
  wherein said plurality of x-ray sources are modulated in time and/or frequency domains by a programmable controller; and
  wherein an algorithmic scheme determines from which of said x-ray sources a detected photon originates.

31. A method of operating a tomographic imaging system, the method of operating a tomographic imaging system comprising:

generating a plurality of x-rays from a plurality of x-ray sources disposed in a plurality of modules arranged in a plurality of geometric shapes, by:
  emitting photons from a plurality of illumination sources disposed in each of said plurality of modules;
  generating electrons from each of a plurality of metallic photocathodes having non-thermionic electron generation;
  wherein each of said plurality of metallic photocathodes are disposed in each of said plurality of x-ray sources, and each of said plurality of metallic photocathodes which emit said electrons are amplified by one of a plurality of electron multipliers disposed in each of said plurality of x-ray sources;
  generating x-rays from each of a plurality of metallic anode targets disposed in each of said plurality of x-ray sources, each of said plurality of metallic anode targets which receive said amplified electrons from a corresponding one of a plurality of electron multipliers;

detecting said x-rays emitted from each of said plurality of x-ray sources in said plurality of x-ray modules, using a plurality of detectors disposed adjacent to said plurality of modules;

modulating each of said plurality of x-ray sources in time and/or frequency domains using a programmable controller; and implementing an algorithmic scheme to determine which of said x-rays sources from which a detected photon originates, when said plurality of x-ray sources are turned on at said same time.

32. The method of claim 31, the method further comprising:

turning on or off said plurality of x-ray sources to provide a coded pattern and/or temporal sequence of x-ray illumination.

33. The method of claim 32, wherein said coded pattern is used to modulate a radiation dose delivered to each portion of an object to be imaged.

34. The method of claim 32, wherein when multiple of said plurality of x-ray sources are turned on at a same time in a ring geometry of said plurality of modules, fields of view of said plurality of x-ray sources do not overlap, and any non-overlapped projections are acquired simultaneously.

35. The method of claim 34, wherein each of said x-ray sources allows encoding of any arbitrary waveform in an X-ray domain.

36. The method of claim 34, wherein illumination from said plurality of x-ray sources is disjointed in time.

37. The method of claim 34, wherein said partitioning scheme allows for blind source separation of said plurality of x-ray sources illuminating a same detector of said plurality of detectors.

38. The method of claim 33, wherein each of said plurality of sources is operated at one of a plurality of frequencies which distinguishes overlapping signals received by a detector from a plurality of detectors.

39. The method of claim 31, the method further comprising:

combining said plurality of modules with other imaging systems to achieve ultra-low dose radiographic imaging.

40. The method of claim 31, the method further comprising:

providing, in real-time, response times and a current draw of each of said illumination sources.

41. The method of claim 31, the method further comprising:

modulating said x-rays by controlling said generation of electrons in each of said plurality of sources, using a control computer;

wherein said control by said control computer is accomplished by enabling individual control and high-frequency pulsing of each of said plurality of x-ray sources.

42. The method of claim 31, wherein recording of images of an object to be imaged, is performed by said plurality of x-ray sources from multiple angles simultaneously, to reduce a scan time or a delivered radiation dose through under-sampled acquisition sequences.

43. The module of claim 14, wherein each said target that partially extends outside of said vacuum manifold is directly cooled by conduction or convection.

* * * * *